United States Patent
Upsher

[19]

[11] Patent Number: 5,846,186
[45] Date of Patent: Dec. 8, 1998

[54] ENDOSCOPE SYSTEM AND COUPLING ARRANGEMENT FOR USE THEREWITH

[75] Inventor: Michael S. Upsher, Los Angeles, Calif.

[73] Assignee: Mercury Enterprises, Inc., Clearwater, Fla.

[21] Appl. No.: 719,038

[22] Filed: Sep. 24, 1996

[51] Int. Cl.[6] ........................................ A61B 1/26
[52] U.S. Cl. ................... 600/185; 600/188; 600/112
[58] Field of Search ............................ 600/185, 186, 600/187, 188, 189, 190, 191, 192, 193, 194, 195, 196, 197, 198, 199, 112; 354/62

[56] References Cited

U.S. PATENT DOCUMENTS

| | | | |
|---|---|---|---|
| 3,900,021 | 8/1975 | Makepeace et al. | 600/112 |
| 4,305,386 | 12/1981 | Tawara | 600/112 |
| 4,318,395 | 3/1982 | Tawara | 600/112 |
| 4,323,304 | 4/1982 | Ishii | 600/112 X |
| 4,413,278 | 11/1983 | Feinbloom | 600/112 X |
| 4,437,458 | 3/1984 | Upsher | 600/106 X |
| 4,807,594 | 2/1989 | Chatenever | 600/112 |
| 4,844,071 | 7/1989 | Chen et al. | 600/112 |
| 5,101,807 | 4/1992 | Kawashima | 600/112 |
| 5,498,230 | 3/1996 | Adair | 600/112 |
| 5,591,119 | 1/1997 | Adair | 600/114 |

*Primary Examiner*—Beverly M. Flanagan
*Attorney, Agent, or Firm*—James E. Larson; Larson & Larson, P.A.

[57] ABSTRACT

There is disclosed herein an endoscope system which includes an endoscope, specifically a laryngoscope, having a handle, a blade connected with the handle and means including an optical eyepiece through which an area immediately in front of the distal end of the blade may be viewed along the optical axis of the eyepiece. The system also utilizes an arrangement including a camera and monitor for displaying the area immediately in front of the blade when the camera is mounted to the eyepiece. A coupling member connectable to the camera is provided for mounting the camera to the eyepiece and locking means forming part of the coupling member and part of the eyepiece is provided for preventing the coupling member and therefore the camera from rotating in a plane normal to the optical axis of the eyepiece and for preventing the coupling member and therefore the camera from rocking in a plane parallel with the optical axis.

11 Claims, 2 Drawing Sheets

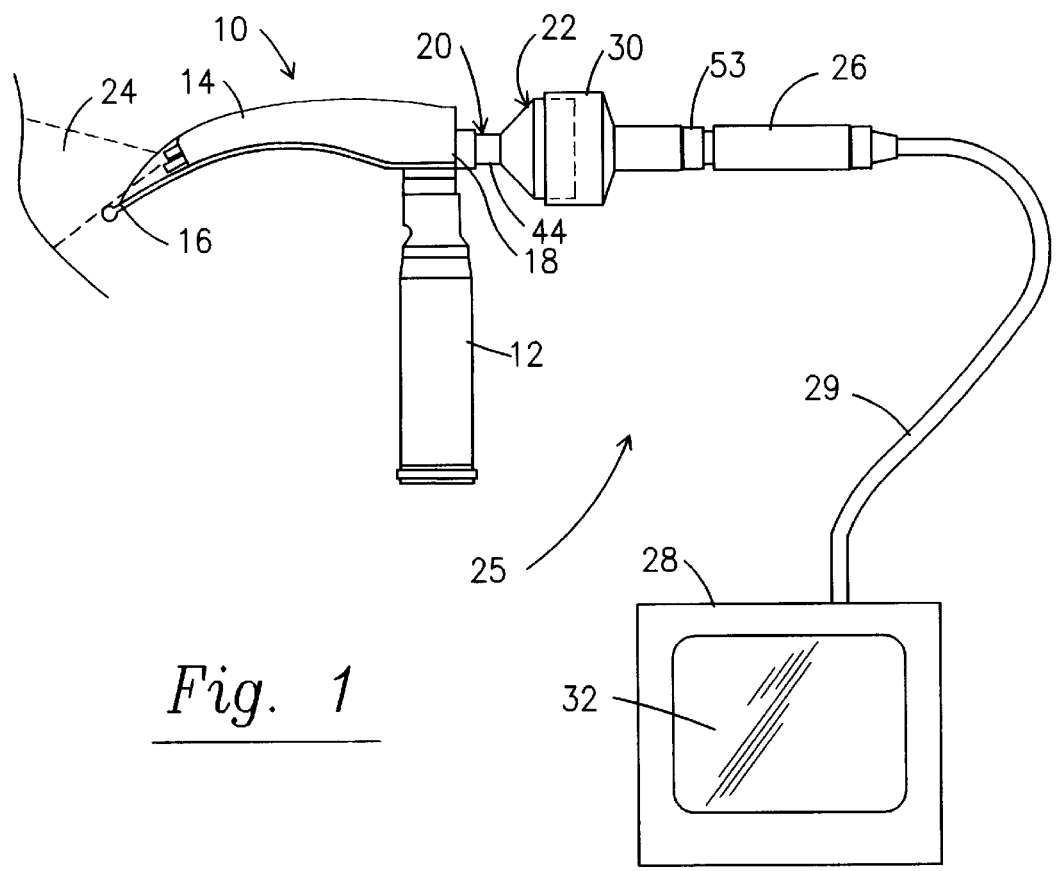
Fig. 1
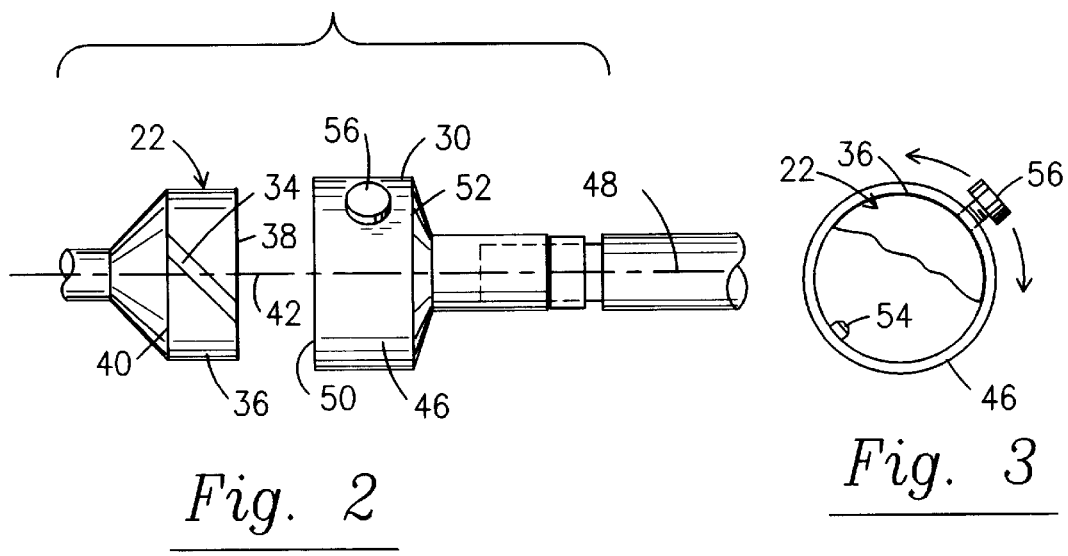
Fig. 2
Fig. 3

ENDOSCOPE SYSTEM AND COUPLING ARRANGEMENT FOR USE THEREWITH

BACKGROUND OF THE INVENTION

The present invention relates generally to endoscope systems in which an endoscope forming part of the system includes an eyepiece which is to be connected with a camera, and more particularly to a specifically configured coupling arrangement for connecting the camera to the eyepiece in a reliable and yet uncomplicated and economical way.

One specific type of endoscope to which the present invention is directed is a laryngoscope, an example of which is illustrated in FIG. 1. This laryngoscope, which is generally designated by the reference numeral 10 is shown in FIG. 1 including a handle 12 and a blade 14 which is mounted to the handle and which includes a distal end 16 and a proximal end 18 closer to the handle than the distal end. An optical arrangement generally indicated at 20 and including an optical eyepiece 22 is connected to and forms part of overall blade 14. The optical arrangement is designed so that an area 24 immediately in front of the distal end of the blade may be viewed through the eyepiece along the optical axis of the eyepiece.

Still referring to FIG. 1, laryngoscope 10 is shown comprising part of an overall laryngoscope system 25 which includes a camera 26 connected with a monitor 28 by means of a cord 29 and a coupling member 30 for connecting the camera to eyepiece 22, as well as other suitable means which may be necessary to allow the area 24 immediately in front of the distal end of blade 14 to be displayed on screen 32 of monitor 28 via the eyepiece 30 and camera 26. In this way, an anesthesiologist using the laryngoscope to intubate a tube into a patient's larynx may view the process indirectly by means of monitor 28 rather than directly by means of eyepiece 22. With the exception of coupling member 30 and a mechanical variation of eyepiece 22, overall system 25 is one which is known in the prior art and therefore will not be described any further herein.

As will be seen hereinafter, the present invention relates specifically to a particularly configured coupling member 30 and an eyepiece 22 which has been mechanically designed to be compatible with the coupling member and to that extent forms part of the present invention. Heretofore, previously used coupling members have had a number of drawbacks. First, most have been relatively complex opto-mechanical devices combining the focusing function with a mechanical connecting means. The mechanical connecting means occasionally functioned in the manner of one or more set screws which served to fairly adequately prevent the coupling and therefore the camera from rotating in a plane normal to the optical axis of the eyepiece. Not all such devices have such set screws. However, according to applicant, this prior art approach does not address adequately the need to prevent the camera from rocking in a plane parallel with and/or along the axis of the eyepiece. As a result, there is a tendency for the image at display 28 to rotate as the laryngoscope is being used disorienting the view. As will be seen hereinafter, the present invention overcomes this drawback in an uncomplicated, economical and reliable manner.

SUMMARY OF THE INVENTION

As will be described in more detail hereinafter, an endoscope system and particularly a laryngoscope system designed in accordance with the present invention is disclosed herein. This endoscope system includes an endoscope, particularly a laryngoscope in the embodiment illustrated, having a handle, a blade connected with the handle, which blade has a distal end and a proximal end closer to the handle than the distal end, and means including an optical eyepiece through which an area immediately in front of the distal end of the blade may be viewed along the optical axis of the eyepiece. This system also comprises means including a camera and monitor for displaying the area immediately in front of the distal end of the blade when the camera is mounted to the eyepiece and a coupling member. In accordance with the present invention, the system still further comprises locking means forming part of the coupling member and part of the eyepiece for preventing the coupling member and therefore the camera from rotating in a plane normal to the optical axis of the eyepiece and for preventing the camera from rocking in a plane parallel with the optical axis.

In a specific embodiment of the present invention, the locking means includes (1) a groove which is disposed within either the eyepiece or the coupling member and which extends along a path defining an acute angle with the parallel plane, and (2) a pin on either the eyepiece or coupling member, whichever one does not contain the groove, the pin being configured to be tightly but slideably received by the groove such that engagement of the pin against the side walls of the groove prevents the coupling member and therefore the camera from rocking in the plane parallel with the optical axis. In this particular embodiment, the angle of the groove is such that engagement of the pin against the side walls of the groove also prevents the coupling member and therefore the camera from rotating in a plane normal to the optical axis. In the same embodiment, the locking means includes a set screw which is separate and distinct from the groove and pin combination for aiding in preventing the coupling member and therefore the camera from rotating in the normal plane.

Still referring to the particular embodiment described immediately above, the groove in this particular embodiment is disposed within the eyepiece rather than the coupling member and it is disposed in a flush or recessed manner so as to allow the eyepiece to function with other components not requiring the groove, as if the groove were not there.

BRIEF DESCRIPTION OF THE DRAWING

The present invention will be described in more detail hereinafter in conjunction with the drawing, wherein;

FIG. 1 is a diagrammatic illustration of an overall laryngoscope system including an eyepiece, a camera and a coupling arrangement for connecting the two together, which system is designed in accordance with the present invention;

FIG. 2 is an enlarged diagrammatic illustration, in side elevational view, of the eyepiece and coupling member forming part of the overall system of FIG. 1;

FIG. 3 diagrammatically illustrates one particular way in which the eyepiece and coupling member are interlocked to one another;

DETAILED DESCRIPTION OF THE DRAWINGS

Figure 4:
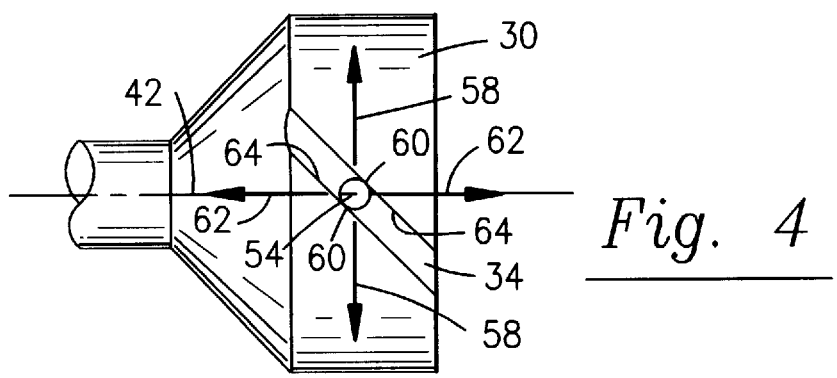
FIG. 4 diagrammatically illustrates a second way in which the eyepiece and coupling member are interlocked to one another.

Turning now to the drawing, wherein like components are designated by like reference numerals throughout the various figures, attention is immediately directed to FIGS. 2–4 in as much as FIG. 1 has been described previously. As indicated above, with the exception of eyepiece 22 and coupling member 30 forming part of overall laryngoscope system 25, this system is known in the prior art. The eyepiece itself and coupling member 30 are illustrated in FIGS. 2–4. With one exception, the eyepiece 22 is known in the prior art. The exception resides in the provision of a slanted groove 34 which extends across the outer circumferential surface 36 of the eyepiece from the front axial edge 38 to or stopping short of a rearward axial edge 40, both edges of which circumscribe the optical axis 42 of the eyepiece. In this particular embodiment illustrated, groove 34 extends across surface 36 in a plane which contains an axis normal to axis 42 and which extends at a 45° angle with the axis 42. The back axial edge 40 of eyepiece 22 is suitably and readably fixedly connected to a cooperating light guide 44 (see FIG. 1), for example and optical fiber, extending along laryngoscope blade 14 such that the light guide's forward most end looks onto viewing area 24. Of course other types of viewing means may be provided.

Coupling member 30 includes a circumferential shell or housing 46 which defines its own axis 48 and which includes an unconnected front axial edge 50 and a back axial edge portion 52 suitably disengagably connectable, for example by means of a friction or screw fit, to camera 26, as generally indicated at 54 in FIG. 1. Shell 46 is sized to slideably but closely fit over surface 36 of eyepiece 22 when axes 42 and 48 are aligned with one another, as best illustrated in FIG. 2.

Turning specifically to FIG. 3, eyepiece 36 is shown positioned within shell 46 of coupling member 30. Coupling member 30 is also shown including a pin 54 fixedly mounted to the inner surface of shell 46 so as to extend radially inwardly therefrom. Coupling member 30 also includes a set screw 56 thread mounted through shell 46 by means of a cooperating threaded through hole within the shell, preferably at a location diametrically opposite that of pin 54. While only one set screw is shown, more than one could be produced around the shell.

In actual practice, the coupling member 30 is positioned over the eyepiece 22 such that pin 54 extends into groove 34. This is carried out with the set screw 56 positioned in its position entirety outside the inner surface of shell 46. Thereafter, once the eyepiece is disposed entirely within the coupling member such that pin 54 resides approximately in the center of groove 34, the set screw 56 is tightened down such that its innermost edge engages tightly against the outermost surface of shell 46. The set screw serves to prevent the coupling member and therefore the camera 26 from rotating about aligned axes 42 and 48. At the same time, pin 54 also prevents the coupling member and therefore the camera from rotating about axis 48 in accordance with the present invention and, also in accordance with the present invention, it prevents the coupling member and therefore the camera from rocking in a plane through the axis 42 or disengaging.

The way in which pin 54 functions to prevent the coupling member from both rotating and rocking is best illustrated in FIG. 4 which shows the pin engaged within slot 34. Note specifically that any attempt to rotate the coupling member, as indicated by arrows 58 is met with resistance from the side walls of groove 34 at points 60. At the same time, any attempt to rock the coupling member in the plane of axis 42, as indicated by arrows 62 is met by resistance of the side walls of groove 34 at points 64. Thus, the groove 34, because of its angular placement relative to axes 42 and 48 serves to prevent both rotating and rocking motion. While the 45° angle illustrated is preferable, the angle and location of the groove 34 can vary while achieving the desired results.

Figure 5:
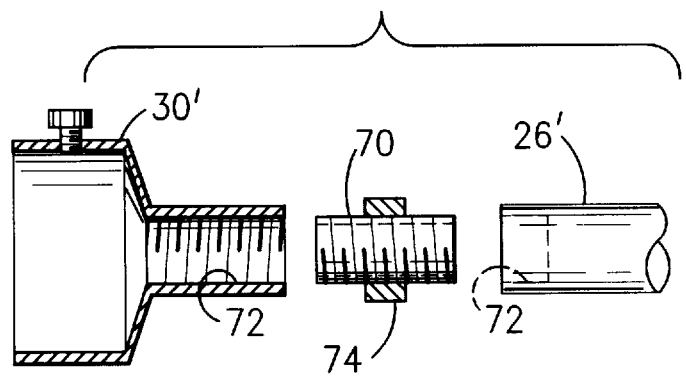
FIGS. 5 and 6 diagrammatically illustrate modifications to the eyepiece and coupling member of FIGS. 1–4.

Turning to FIG. 5, there is shown a modified coupling member 30' and a modified camera 26'. The only difference between these components and the corresponding components 30 and 26 resides in the way they are connected together. In the case of coupling member 30' and camera 26' they are connected together using a threaded connecting bolt 70 thread connectable at opposite ends to cooperating threaded openings 72 in the coupling member and camera. A lock nut 74 threaded over the bolt is used to hold the camera in place, that is, preventing it from rotating about its axis. Moreover, this locknut can be used to adjust the rotational orientation of the camera about its axis and, in this way, adjust the orientation of the image on the monitor. The bolt could be separate from either the coupling member and camera as shown or it could be a permanent part of either, but most preferably the coupling member. Assuming the latter, the threaded opening 72 in the camera could and probably would be formed within a separate component which would be connected to the camera 26 in the same way as coupling member 30.

Figure 6:
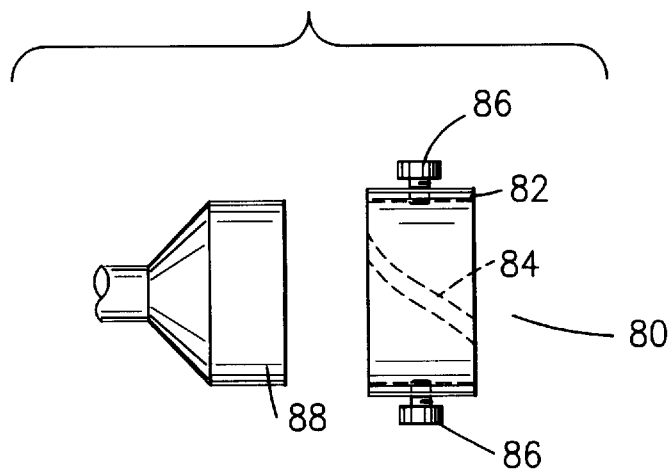

Returning to FIGS. 2–4, eyepiece 22 was described as forming part of the overall endoscope and including its own groove 34. It is to be understood that the present invention is equally applicable to the utilization of a separate and distinct adapter ring which includes its own groove and which is configured to fit over an eyepiece that does not such a groove. FIG. 6 illustrates such an adapter which is generally designated by the reference numeral 80 and which includes and adapter 82 ring having a groove 84 corresponding to previously described groove 34 and two or more set screws 86 extending through the ring at circumferentially spaced points . This adapter is sized to fit over an eyepiece 88 corresponding to eyepiece 22 but one which does not include groove 34.

What is claimed is:

1. A laryngoscope system, comprising:
   (a) a laryngoscope including a handle, a blade connected with the handle and having a distal end and a proximal end closer to the handle than the distal end, and means including an optical eyepiece through which an area immediately in front of the distal end of the blade may be viewed along an optical axis of the eyepiece;
   (b) means including a camera and monitor for displaying said area when the camera is mounted to said eyepiece; and
   (c) a coupling member connectable to said camera for mounting the camera to said eyepiece;
   (d) first locking means including a set screw mounted for axial movement on either said coupling member or eyepiece for preventing said coupling member and therefore said camera from rotating in a plane normal to the optical axis of the eyepiece and a second locking means including (i) a groove disposed within either said eyepiece or said coupling member and extending along a path defining an acute angle with a plane parallel to the optical axis of the eyepiece and (ii) a pin on either said eyepiece or coupling member, whichever does not contain said groove, said pin being configured to be tightly but slidably received by said groove such that engagement of the pin against the side walls of said groove prevents said coupling member and therefore said camera from rocking in a plane parallel with said optical axis.

2. A system according to claim 1 wherein said acute angle is 45°.

3. An system according to claim 1 wherein said groove is disposed on said eyepiece, said groove being inset with respect to an external surface of the eyepiece so as not to inhibit cooperation of said surface with other components besides said coupling member, which other components do not require the use of said groove.

4. A system according to claim 1 wherein said groove is disposed within said eyepiece, said groove being inset with respect to an external surface of the eyepiece so as not to inhibit cooperation of said surface with other components besides said coupling member, which other components do not require the use of said groove.

5. A system according to claim 1 including means for adjustably locking the camera in a fixed rotational position about said optical axis, whereby to adjustably fix the orientation of the area displayed.

6. A system according to claim 5 wherein said coupling member includes a male threaded bolt, wherein said camera includes means defining a female threaded component for receiving said male threaded component, and wherein said coupling member includes a lock nut thread mounted around said male threaded member and serving as said adjustable locking means.

7. An endoscope system, comprising;
  (a) an endoscope including a blade having a distal end and a proximal end and means including an optical eyepiece through which an area immediately in front of the distal end of the blade may be viewed along the optical axis of said eyepiece;
  (b) means including a camera and monitor for displaying said area when the camera is mounted to said eyepiece;
  (c) a coupling member connectable to said camera for mounting the camera to said eyepiece; and
  (d) means forming part of said coupling member and part of said eyepiece for preventing said coupling member and therefore said camera from rotating in a plane normal to the optical axis of the eyepiece and for preventing said camera from rocking in a plane parallel with said axis, said locking means including (i) a groove disposed within said eyepiece and extending along a path defining an acute angle with said parallel plane, said groove being inset with respect to an external surface of the eyepiece so as not to inhibit cooperation of said surface with other components besides said coupling member, which other components do not require the use of said groove, and (ii) a pin on the coupling member, said pin being configured to be tightly but slidably received by said groove such that engagement of the pin against the side walls of the groove prevents said coupling member and therefore said camera from rotating in said plane normal to said optical axis and for preventing said camera from rocking in said plane parallel with said optical axis.

8. (amended) A system according to claim 7 wherein said acute angle is 45°.

9. A system according to claim 8 wherein said endoscope is a laryngoscope.

10. A system according to claim 8 wherein said locking means includes a set screw mounted for axially movement on said coupling member for engagement against said eyepiece, whereby to aid in preventing said coupling member and therefore said camera from rotating in said plane normal to said optical axis.

11. An endoscope system, comprising;
  (a) an endoscope including a blade having a distal end and a proximal end and means including an optical eyepiece through which an area immediately in front of the distal end of the blade may be viewed along the optical axis of said eyepiece;
  (b) means including a camera and monitor for displaying said area when the camera is mounted to said eyepiece;
  (c) a coupling member connectable to said camera for mounting the camera to said eyepiece;
  (d) an adapter ring disengagably connectable to said camera for mounting the camera to said eyepiece;
  (e) locking means forming part of said coupling member and part of said adapter ring for preventing said coupling member and therefore said camera from rotating in a plane normal to the optical axis of the eyepiece and for preventing said camera from rocking in a plane parallel with said optical axis, said locking means including (i) a straight groove disposed within said adapter ring and extending along a path defining an acute with said parallel plane, and (ii) a pin on said coupling member, said pin being configured to be tightly but slidably received by said groove such that engagement of the pin against the side walls of the groove prevents said coupling member and therefore said camera from rotating in said plane normal to said optical axis and for preventing said camera from rocking in said plane parallel with said optical axis.

\* \* \* \* \*